United States Patent [19]

Ohnishi et al.

[11] Patent Number: 5,130,483

[45] Date of Patent: Jul. 14, 1992

[54] ISOPRENOID DERIVATIVES AND PHARMACEUTICAL PREPARATIONS CONTAINING THE SAME

[75] Inventors: Hiroyuki Ohnishi; Shingo Koyama; Ryoichi Nanba; Syozo Miyaoka, all of Tokyo; Akira Masuda, Hokkaido; Yoshiyuki Shikata, Chiba; Hideto Ushijima; Seiitsu Murota, both of Tokyo, all of Japan

[73] Assignee: Terumo Kabushiki Kaisha, Tokyo, Japan

[21] Appl. No.: 460,335

[22] PCT Filed: Oct. 14, 1988

[86] PCT No.: PCT/JP88/01046

§ 371 Date: May 18, 1990

§ 102(e) Date: May 18, 1990

[87] PCT Pub. No.: WO89/03375

PCT Pub. Date: Apr. 20, 1989

[30] Foreign Application Priority Data

Oct. 16, 1987 [JP] Japan .................. 62-259512
Dec. 23, 1987 [JP] Japan .................. 62-325734
Jan. 19, 1988 [JP] Japan .................... 63-9020

[51] Int. Cl.$^5$ .................. C07C 233/00; C07C 45/00
[52] U.S. Cl. ........................ 564/170; 570/075; 568/308
[58] Field of Search ............ 560/75; 564/170, 308; 514/622, 678

[56] References Cited

U.S. PATENT DOCUMENTS 4,618,627 10/1986 Murase et al. ............... 514/678
4,673,684  6/1987 Wakabayashi et al. ...... 514/327
4,733,002  3/1988 Yokoyama et al. ........... 560/055

FOREIGN PATENT DOCUMENTS 61-118346 5/1986 Japan .

OTHER PUBLICATIONS

CA108(3):19241z 1987 [Wollenweber, E. et al., Z Naturforsch C:Biosci 42(9-10) 1030-4 1987].
Hashimoto et al., *Zeitschrift fur Naturfarsehung* 43:470-472 (1988).
*Patent Abstracts of Japan*, vol. 10, No. 226 (C-364) [2282] (1986).
*Patent Abstracts of Japan*, vol. 9, No. 309 (C-318) [2032] (1985).
*Patent Abstracts of Japan*, vol. 13, No. 427 (C-639) [3775] (1989).
*Patent Abstracts of Japan*, vol. 13, No. 472 (C-647) [3820] (1989).

*Primary Examiner*—Paul J. Killos
*Attorney, Agent, or Firm*—Burns, Doane, Swecker & Mathis

[57] ABSTRACT

Isoprenoid derivatives represented by the general formula (I)

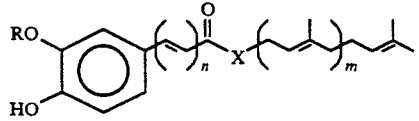

wherein R represents a hydrogen atom or a lower alkyl group, X represents —$CH_2$—, —O— or —NH—, n represents number of the double bond in trans-configuration and is 1 or 2, and m is an integer from 0 to 3.

The compounds have a 5-lipoxygenase-inhibiting activity and are useful as a therapeutic agent for such diseases as allergy, nephritis, hepatitis, rheumatism and gastric ulcer.

30 Claims, No Drawings

ISOPRENOID DERIVATIVES AND PHARMACEUTICAL PREPARATIONS CONTAINING THE SAME

TECHNICAL FIELD

The invention relates to novel isoprenoid derivatives and 5-lipoxygenase-inhibitors and anti-ulcer agents containing the same. The isoprenoid derivatives of the invention have an inhibitory activity against 5-lipoxygenase as well as an anti-ulcer activity.

TECHNOLOGICAL BACKGROUND

Leukotrienes such as leukotriene $C_4$ ($LTC_4$) and leukotriene $D_4$ ($LTD_4$) which participate in the onset mechanism of allergy are biosynthesized from arachidonic acid by the action of 5-lipoxygenase.

It has recently been made evident that leucotrienes relates not only to the onset of allergy, but also to the onset of other pathological conditions including nephritis, hepatis, leumatism and gastric ulcer.

Accordingly, it has been a subject of investigation to find substances inhibiting biosynthesis of leucotrienes thereby being effective in the therapy of these diseases. Discovery of substances having anti-ulcer activities against gastric and other ulcers has also been another subject.

We synthesized a variety of isoprenoid derivatives and made extensive studies on 5-lipoxygenase-inhibiting activities and anti-ulcer activities of these compounds. As a result of these studies we have found that the isoprenoid derivatives according to the present invention possess a high 5-lipoxygenase-inhibiting activity and a potent anti-ulcer activity. The invention has been completed on the basis of the finding. The 5-lipoxygenase inhibitory isoprenoid derivatives of the invention inhibit the biosynthesis of leucotrienes thereby being useful in the therapy of nephritis, hepatitis and rheumatism as well as asthma and rhinitis which are allergic diseases.

Furthermore, the isoprenoid derivatives of the invention which have an anti-ulcer activity are also useful in the therapy of gastric and other ulcers.

It is therefore an object of the invention to provide new isoprenoid derivatives and 5-lipoxygenase inhibitors and anti-ulcer agents containing same.

DISCLOSURE OF THE INVENTION

To meet the above-mentioned object, the invention provides isoprenoid derivatives represented by the general formula (I)

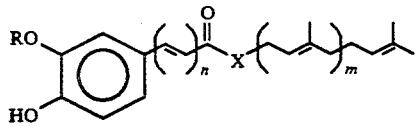

(I)

wherein R represents a hydrogen atom or a lower alkyl group, X represents $-CH_2-$, $-O-$ or $-NH-$, n represents number of the double bond in trans-configuration and is 1 or 2 and m is an integer from 0 to 3.

As examples of the above lower alkyl group are mentioned methyl, ethyl, n-propyl, i-propyl, n-butyl and the like. Methyl is most preferable.

The isoprenoid derivatives represented by the formula (I) are prepared selectively by the methods described below depending upon the nature of the group X.

1) The compounds of the formula (I) wherein X is $-CH_2-$ are produced by reacting an aldehyde derivative having the formula (II)

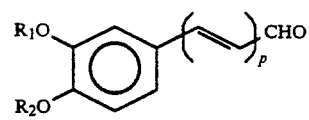

(II)

wherein $R_1$ represents a group defined above for R or a hydroxy-protecting group, $R_2$ represents a hydrogen atom or a hydroxy-protecting group and p represents number of the double bond in trans-configuration and is 0 or 1 with an isoprenylacetone having the formula (III)

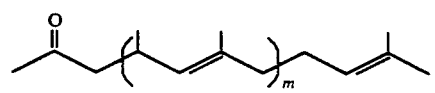

(III)

wherein m has the same meaning as defined above followed by a dehydration reaction and a protective group-eliminating reaction.

2) The compounds of the formula (I) wherein X is $-O-$ are produced by reacting a carboxylic acid derivative having the formula (II)′

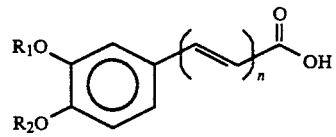

(II)′ wherein $R_1$, $R_2$ and n have the same meanings as defined above with an isoprenyl alcohol having the formula (III)′

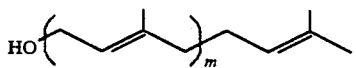

(III)′ wherein m has the same meaning as defined above followed by a protective group-eliminating reaction.

3) The compounds of the formula (I) wherein X is $-NH-$ are produced by reacting a carboxylic acid derivative having the formula (II)′ with an isoprenyl amine having the formula (III)″

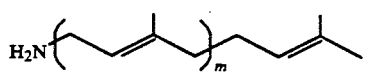

(III)″ wherein m has the same meaning as defined above followed by a protective group-eliminating reaction. The isoprenyl amines mentioned above are produced by decomposing a corresponding isoprenyl phthalimide with hydrazine.

As the hydroxy-protecting group in the above reactions is preferably employed a lower alkoxy-lower alkyl group such as methoxymethyl, ethoxymethyl or methoxyethyl, a tetrahydropyranyl group or the like. The reaction between the compound (II) and the compound (III) and the reaction between the compound (II)′ and the compound (III)' or (III)" are a condensation reaction which is carried out by a conventional method. For example, the reaction is carried out by allowing the reactants to contact in an inert organic solvent such as tetrahydrofuran or methylene chloride at −78° C. to room temperature for 10 min. to 5 hours. The reaction product is recovered from the reaction mixture by a conventional procedure. The hydroxy-protecting group can be eliminated by a conventional means such as by contacting with an acid.

The isoprenoid derivatives of the invention are used as a 5-lipoxygenase inhibitor or as an anti-ulcer agent. The dosage is variable depending upon symptoms and are generally 10–2000 mg and preferably 20–600 mg per day in adults, which may be divided into 1–3 doses as required by the symptoms. The administration may be in any suitable form and is desirably by oral route. Intravenous administration is also acceptable.

The compounds of the invention are used as the only active ingredient or as one of the active ingredients, either alone or in admixture with pharmaceutical carriers or excipients, and can be applied in various forms of pharmaceutical preparation such as tablets, sugar-coated tablets, powders, capsules, granules, suspension, emulsion or injectable solution. The carrier or excipient includes calcium carbonate, calcium phosphate, starch, glucose, lactose, dextrin, alginic acid, mannitol, talc, magnesium stearate and the like.

The invention will be described in more detail with reference to examples and test examples. They are, however, not intended to limit the invention in any way.

EXAMPLE 1

In 40 ml of dry tetrahydrofuran is dissolved 1.25 g of diisopropylamine under an argon atmosphere. To the solution cooled to −15° C. is added 8.00 ml of 1.6 M hexane solution of n-butyllithium, and the mixture is stirred for 10 min. To the resulting mixture is added dropwise a solution of 1.56 g of prenylacetone in 10 ml of dry tetrahydrofuran at −15° C. followed by stirring for 10 min. To the reaction mixture cooled to −78° C. is dropwise added a solution of 2.50 g of 3'-methoxy-4'-methoxymethyloxycinnamaldehyde in 10 ml of dry tetrahydrofuran, and the mixture is stirred at −78° C. for 20 min. To the reaction mixture is added saturated aqueous sodium chloride, and the organic layer is separated. The aqueous layer is extracted with ethyl acetate, and the organic layer is washed with 2N hydrochloric acid, a saturated aqueous solution of sodium hydrogen carbonate and saturated aqueous sodium chloride and dried over anhydrous magnesium sulfate. The solvent is distilled off under reduced pressure, and the residue is subjected to column chromatography on silica gel. From the fraction eluted with chloroform is obtained 1.93 g of 3-hydroxy-1-(3'-methoxy-4'-methoxymethyloxyphenyl)-9-methyl1,8-decadien-5-one which is an aldol adduct.

1.93 g of the aldol adduct is dissolved in 50 ml of methanol. To the solution is added 10 ml of 6N hydrochloric acid, and the mixture is stirred at room temperature for 5 hours. The methanol is distilled off under reduced pressure followed by addition of saturated aqueous sodium chloride and then extraction with methylene chloride. The organic layer is washed with saturated aqueous sodium chloride and dried over anhydrous magnesium sulfate. The solvent is distilled off under reduced pressure, and the residue is subjected to column chromatography on silica gel. From the fraction eluted with methylene chloride is obtained 1.25 g of 1-(4'-hydroxy-3'-methoxyphenyl)-9-methyl-1,3,8-decatrien-5-one (1). Spectroscopic data of the product support the structure of the formula (1) below.

NMR (CDCl₃)δ: 1.51–1.80(6H.m), 3.89 (3H.s), 5.07 (1H, br, t, J=6Hz), 6.15(1H.d.J=15 Hz)

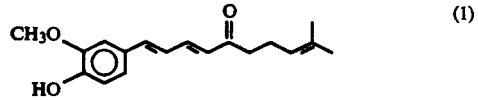

EXAMPLE 2

In 20 ml of dry tetrahydrofuran is dissolved 0.73 g of diisopropylamine under an argon atmosphere. To the solution cooled to −15° C. is added 4.65 ml of 1.6 M hexane solution of n-butyllithium, and the mixture is stirred for 10 min. To the resulting mixture is added dropwise a solution of 1.40 g of geranylacetone in 5 ml of dry tetrahydrofuran at −15° C. followed by stirring for 10 min. To the reaction mixture cooled to −78° C. is dropwise added a solution of 1.46 g of 3'-methoxy-4'-methoxymethyloxycinnamaldehyde in 5 ml of dry tetrahydrofuran, and the mixture is stirred at −78° C. for 40 min. To the reaction mixture is added saturated aqueous sodium chloride, and the organic layer is separated. The aqueous layer is extracted with ethyl acetate, and the organic layer is washed with 2N hydrochloric acid, a saturated aqueous solution of sodium hydrogen carbonate and saturated aqueous sodium chloride and dried over anhydrous magnesium sulfate. The solvent is distilled off under reduced pressure, and the residue is subjected to column chromatography on silica gel. From the fraction eluted with hexane-methylene chloride (1:1 v/v) is obtained 1.31 g of 9,13-dimethyl-3-hydroxy-1-(3'-methoxy-4'-methoxymethyloxyphenyl)-1,8,12-tetradecatrien-5-one.

1.23 g of the aldol adduct is dissolved in 40 ml of methanol. To the solution is added 10 ml of 6N hydrochloric acid, and the mixture is stirred at room temperature for 4 hours. The methanol is distilled off under reduced pressure followed by addition of saturated aqueous sodium chloride and then extraction with methylene chloride. The organic layer is washed with saturated aqueous sodium chloride and dried over anhydrous magnesium sulfate. The solvent is distilled off under reduced pressure, and the residue is subjected to column chromatography on silica gel. From the fraction eluted with hexane-methylene chloride (1:1 v/v) is obtained 0.75 g of 9,13-dimethyl-1-(4'-hydroxy-3'-methoxyphenyl)-1,3,8,12-tetradecatetraen-5-one (2). Spectroscopic data of the product support the structure of the formula (2) below.

NMR (CDCl₃)δ:
1.45–1.72(9H, m), 3.86(3H,s), 4.83–5.23(2H,m), 6.12(1H,d, J=15 Hz)

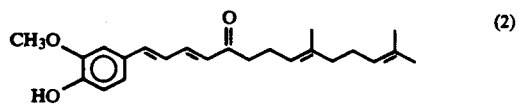

EXAMPLE 3

In 20 ml of dry tetrahydrofuran is dissolved 0.66 g of diisopropylamine under an argon atmosphere. To the solution cooled to −15° C. is added 4.20 ml of 1.6M hexane solution of n-butyllithium, and the mixture is stirred for 10 min. To the resulting mixture is added dropwise a solution of 1.70 g of trans,trans-farnesylacetone in 5 ml of dry tetrahydrofuran at −15° C. followed by stirring for 10 min. To the reaction mixture cooled to −78° C. is dropwise added a solution of 1.31 g of 3'-methoxy-4'-methoxymethyloxycinnamaldehyde in 5 ml of dry tetrahydrofuran, and the mixture is stirred at −78° C. for 45 min. To the reaction mixture is added saturated aqueous sodium chloride, and the organic layer is separated. The aqueous layer is extracted with ethyl acetate, and the organic layer is washed with 2N hydrochloric acid, a saturated aqueous solution of sodium hydrogen carbonate and saturated aqueous sodium chloride and dried over anhydrous magnesium sulfate. The solvent is distilled off under reduced pressure, and the residue is subjected to column chromatography on silica gel. From the fraction eluted with heane-methylene chloride (1:1 v/v) is obtained 1.54 g of 3-hydroxy-1-(3'-methoxy-4'-methoxymethyloxyphenyl)-9,13,17-trimethyl-1,8,12,16-octadecatetraen-5-one which is an aldol adduct.

1.45 g of the aldol adduct is dissolved in 50 ml of methanol. To the solution is added 10 ml of 6N hydrochloric acid, and the mixture is stirred at room temperature for 5 hours. The methanol is distilled off under reduced pressure followed by addition of saturated aqueous sodium chloride and then extraction with methylene chloride. The organic layer is washed with saturated aqueous sodium chloride and dried over anhydrous mangnesium sulfate. The solvent is distilled off under reduced pressure, and the residue is subjected to column chromatography on silica gel. From the fraction eluted with hexane-methyl chloride (1:1 v/v) is obtained 1.11 g of 1-(4'-hydroxy-3'-methoxyphenyl)-9,13,17-trimethyl-1,3,8,12,16-octadecapentaen-5-one (3). Spectroscopic data of the product support the structure of the formula (3) below.

NMR (CDCl₃)δ:
1.52–1.82(12H,m),3.84(3H,s), 4.88–5.30(3H,m), 6.14(1H,b,J=15.5 Hz)

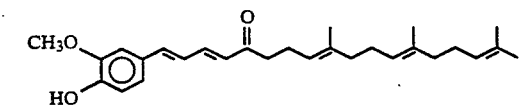

(3)

EXAMPLE 4

In 20 ml of dry tetrahydrofuran is dissolved 0.49g of diisopropylamine under an argon atmosphere. To the solution cooled to −15° C. is added 3.14 ml of 1.6M hexane solution of n-butyllithium, and the mixture is stirred for 10 min. To the resulting mixture is added dropwise a solution of 0.61 g of prenylacetone in 5 ml of dry tetrahydrofuran at −15° C. followed by stirring for 10 min. To the reaction mixture cooled to −78° C. is dropwise added a solution of 1.00 g of 3',4'-dimethoxymethyloxybenzaldehyde in 5 ml of dry tetrahydrofuran, and the mixture is stirred at −78° C. for 20 min. To the reaction mixture is added saturated aqueous sodium chloride, and the organic layer is separated. The aqueous layer is extracted with ethyl acetate, and the organic layer is washed with 2N hydrochloric acid, a saturated aqueous solution of sodium hydrogen carbonate and saturated aqueous sodium chloride and dried over anhydrous magnesium sulfate. The solvent is distilled off under reduced pressure, and the residue is subjected to column chromatography on silica gel. From the fraction eluted with methylene chloride is obtained 0.86 g of 1-(3',4'-dimethoxymethyloxyphenyl)-1-hydroxy-7-methyl-6-octen-3-one which is an aldol adduct.

0.86 g of the aldol adduct is dissolved in 25 ml of methanol. To the solution is added 10 ml of 6N hydrochloric acid, and the mixture is stirred at room temperature for 5 hours. The methanol is distilled off under reduced pressure followed by addition of saturated aqueous sodium chloride and then extraction with methylene chloride. The organic layer is washed with saturated aqueous sodium chloride and dried over anhydrous magnesium sulfate. The solvent is distilled off under reduced pressure, and the residue is subjected to column chromatography on silica gel. From the fraction eluted with methylene chloride is obtained 0.51 g of 1-(3',4'-dihydroxyphenyl)-7-methyl-1,6-octadien-3-one (4). Spectroscopic data of the product support the structure of the formula (4) below.

NMR (CDCl₃)δ: 1.50–1.80(6H,m), 5.07(1H,dr,t,J−6 Hz), 6.42(1H,d,J=16 Hz), 7.38(1H,d,J=16 Hz)

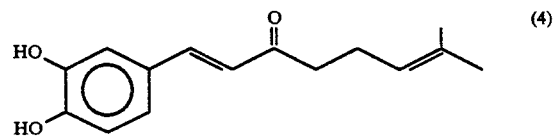

(4)

EXAMPLE 5

In 40 ml of methylene chloride is suspended 2.00 g of ferulic acid under an argon atmosphere. To the suspension cooled to −10° C. are added 2.87 ml of triethylamine and 2.03 ml of ethyl chlorocarbonate. The mixture is stirred for 30 min. followed by addition of a solution of 0.87 g of prenol in 10 ml of methylene chloride. The mixture is stirred at −10° C. to 0° C. for 3 hours. The reaction mixture is poured onto water and extracted with chloroform. The organic layer is washed with saturated aqueous sodium chloride and dried over anhydrous sodium sulfate. The solvent is distilled off under reduced pressure, and the residue is subjected to column chromatography on silica gel. From the fraction eluted with chloroform is obtained 1.78 g of prenyl 4-ethoxycarbonyloxy-3-methoxycinnamate.

In 60 ml of methanol is dissolved 1.78 g of prenyl 4-ethoxycarbonyloxy-3-methoxycinnamate. To the solution is added 15 ml of water followed by addition of 0.56 g of sodium carbonate. The mixture is stirred for 4 hours followed by addition of 100 ml of water and then 1N hydrochloric acid to acidify the mixture. The resulting mixture is extracted with chloroform, and the organic layer is washed with water and saturated aqueous sodium chloride and dried over anhydrous sodium sulfate. The solvent is distilled off under reduced pressure, and the residue is subjected to column chromatography on silica gel. From the fraction eluted with chloroform is obtained 1.02 g of prenyl 4-hydroxy-3-methoxycinnamate (5). Spectroscopic data of the product support the structure of the formula (5) below.

NMR (CDCl₃)δ:

6.30(1H,d,J=15Hz), 4.70(2H,d,J=7 Hz), 4.30(2H,g,J=7Hz), 3.87 (3H,s), 1.8(6H,ds), 1.8(6H,ds), 1.35(3H,t,j=7 Hz)

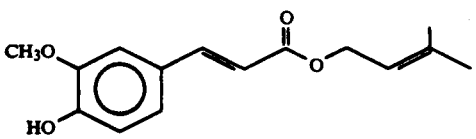 (5)

EXAMPLE 6

To a suspension of 5-(3-methoxy-4-hydroxyphenyl)-2,4-pentadienoic acid (2 g) in methylene chloride (50 ml) is added diisopropylethylamine (6.33 ml) under an argon atmosphere. To the mixture cooled to 0° C. is added chloromethyl methyl ether (2.07 ml), and the resulting mixture is stirred for 3.5 hours.

The reaction mixture is poured onto water followed by addition of 1N hydrochloric acid and extraction with two portions of methylene chloride. The organic layer is washed with a saturated aqueous solution of sodium hydrogen carbonate and dried over anhydrous magnesium sulfate followed by concentration under reduced pressure. The residue is subjected to column chromatography on silica gel. From the fraction eluted with n-hexane-ethyl acetate (2:1 v/v) is obtained 2.72 g of methoxymethyl 5-(3-methoxy4 methoxymethoxyphenyl)-2,4-pentadienoate.

To a solution of methoxymethyl 5-(3-methoxy-4-methoxymethoxyphenyl)-2,4-pentadienoate (2.72 g) in methanol (30 ml) are added water (5 ml) and sodium hydroxide (0.47 g). The mixture is stirred at room temperature for 67.5 hours and then at 60° C. for one hour.

After cooling the reaction mixture, water and 1N hydrochloric acid are added (to a pH of 1 or below), and the mixture is extracted twice with ethyl acetate. The organic layer is washed with saturated aqueous sodium chloride and dried over anhydrous magnesium sulfate and then concentrated under reduced pressure. The residue is subjected to column chromatography on silica gel. From the fraction eluted with methylene chloride is obtained 1.97 g of 5-(3-methoxy-4-methoxymethoxyphenyl)-2,4-pentadienoic acid.

5-(3-Methoxy-4-methoxymethoxyphenyl)-2,4-pentadienoic acid (1.97 g) and 4-dimethylaminopyridine (0.09 g) are dissolved in methylene chloride (40 ml) under an argon atmosphere. To the mixture is added N,N-dicyclohexylcarbodiimide (1.85 g) at 0° C. followed by stirring for 10 min. and then addition of prenol (1.49 ml). The resulting mixture is stirred at room temperature for 23.5 hours.

The reaction mixture is filtered (washed with ether). To the filtrate are added water and then 1N hydrochloric acid followed by extraction with two portions of methylene chloride. The organic layer is washed with a saturated aqueous sodium hydrogen carbonate solution, dried over anhydrous magnesium sulfate and then concentrated under reduced pressure. The residue is subjected to column chromatography on silica gel. From the fraction eluted with n-hexane-ethyl acetate (3:1 v/v) is obtained 2.23 g of prenyl 5-(3-methoxy-4-methoxymethoxyphenyl)-2,4-pentadienoate.

To a solution of prenyl 5-(3-methoxy-4-methoxymethoxyphenyl)-2,4-pentadienoate (2.33 g) in methanol (20 ml) is added p-toluenesulfonic acid (2 microspatulafuls). The mixture is stirred at 50° C. for 7 hours.

The reaction mixture is poured onto a mixture of saturated aqueous sodium chloride and a saturated aqueous sodium hydrogen carbonate solution and extracted twice with ethyl acetate. The organic layer is washed with saturated aqueous sodium chloride, dried over anhydrous magnesium sulfate and then concentrated under reduced pressure. The residue is subjected to column chromatography on silica gel. From the fraction eluted with methylene chloride is obtained 1.38 g of prenyl 5-(3-methoxy-4-hydroxyphenyl)-2,4-pentadienoate (6). Spectroscopic data of the product support the structure of the formula (6) below.

NMR (CDCl₃)δ:
1.73(6H,s), 3.87(3H,s), 4.63(2H,d,J=7 Hz), 5.87(1H,d,J=15 Hz)

 (6)

EXAMPLE 7

To a suspension of protocatechualdehyde (1.93 g) in methylene chloride (50 ml) is added under an argon atmosphere diisopropylethylamine (9.74 ml). To the mixture cooled to 0° C. is added chloromethyl methyl ether (3.18 ml), and the resulting mixture is stirred at room temperature for 39 hours.

The reaction mixture is poured onto water and extracted twice with methylene chloride. The organic layer is washed with aqueous sodium chloride, dried over anhydrous magnesium sulfate and concentrated under reduced pressure. The residue is subjected to column chromatography on silica gel. From the fraction eluted with n-hexane-ethyl acetate (3:1 v/v) is obtained 2.95 g of 3,4-dimethoxymethoxybenzaldehyde.

Triethyl 4-phosphonocrotonate (80%) (4.25 ml) is dropwise added to a solution of potassium tert-butoxide (1.91 g) in dry tetrahydrofuran (30 ml) at −15° C. under an argon atmosphere. The mixture is stirred at −15° C. to −10° C. for 35 min., to which is further added dropwise a solution of 3,4-dimethoxymethoxybenzaldehyde (2.89 g) in dry tetrahydrofuran (15 ml). The resulting mixture is stirred at room temperature for 2 hours.

To the reaction mixture are added a saturated solution of ammonium chloride and 1N hydrochloric acid followed by extraction with two portions of ethyl acetate. The organic layer is washed with a saturated aqueous sodium hydrogen carbonate solution and then with saturated aqueous sodium chloride, dried over anhydrous magnesium sulfate and concentrated under reduced pressure. The residue is subjected to column chromatography on silica gel. From the fraction eluted with n-hexane - ethyl acetate (1:1 v/v) is obtained 3.96 g of ethyl 5-(3,4-dimethoxymethoxyphenyl)-2,4-pentadienoate.

To a solution of ethyl 5-(3,4-dimethoxymethoxyphenyl)-2,4-pentadienoate (3.96 g) in methanol (30 ml) are added water (5 ml) and potassium hydroxide (86%) (1.04 g). The mixture is stirred at room temperature for 2.5 hours and then at 60° C. for 3 hours.

To the reaction mixture, after cooled, are added water and 1N hydrochloric acid (to a pH of 1 or below), and the mixture is extracted three times with ethyl acetate. The organic layer is washed with saturated aqueous sodium chloride, dried over anhydrous magnesium sulfate and then concentrated under reduced pressure. The residue is subjected to column chromatography on silica gel. From the fraction eluted with methylene chloride is obtained 3.26 g of 5-(3,4-dimethoxymethoxyphenyl)-2,4-pentadienoic acid.

5-(3,4-dimethoxymethoxyphenyl)-2,4-pentadienoic acid (3.23 g) and 4-dimethylaminopyridine (0.13 g) are dissolved in methylene chloride (50 ml) under an argon atmosphere. To the mixture is added N,N-dicyclohexylcarbodiimide (2.72 g) at 0° C. followed by stirring for 5 min. and then addition of prenol (1.32 ml). The resulting mixture is stirred at room temperature for 21 hours.

The reaction mixture is poured onto water and extracted with two portions of methylene chloride. The organic layer is washed with saturated aqueous sodium chloride, dried over anhydrous magnesium sulfate and then concentrated under reduced pressure. The residue is subjected to column chromatography on silica gel. From the fraction eluted with n-hexane-ethyl acetate (2:1 v/v) is obtained 3.24 g of prenyl 5-(3,4-dimethoxymethoxyphenyl)-2,4-pentadienoate.

To a solution of prenyl 5-(3,4-dimethoxymethoxyphenyl)-2,4-pentadienoate (3.24 g) in methanol-water (4:1)(25 ml) is added p-toluenesulfonic acid (2 microspatulafuls). The mixture is stirred at 50° C. for 5 hours.

The reaction mixture is poured onto a mixture of saturated aqueous sodium chloride and a saturated aqueous sodium hydrogen carbonate solution and extracted twice with ethyl acetate. The organic layer is washed with saturated aqueous sodium chloride, dried over anhydrous magnesium sulfate and then concentrated under reduced pressure. The residue is subjected to column chromatography on silica gel. From the fraction eluted with methylene chloride-methylene chloride : methanol (200:1) is obtained 1.29 g of prenyl 5-(3,4-dihydroxyphenyl)-2,4-pentadienoate (7).

Spectroscopic data of the product support the structure of the formula (7) below.

NMR (CDCl$_3$)δ:
1.74(6H,s), 4.63(2H,d,J=7 Hz), 5.84(1H,d,J=15 Hz)

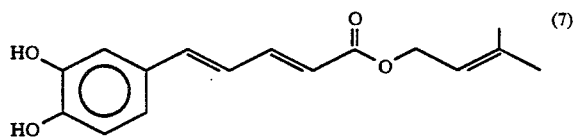

(7)

EXAMPLE 8

Under a nitrogen atmosphere, to a solution of 1.74 ml of ethyl chlorocarbonate in 60 ml of dry methylene chloride is added dropwise under ice-cooling a solution of 2 g of 5-(4-hydroxy-3-methoxyphenyl)-2,4-pentadienoic acid in 2.53 ml of triethylamine and 20 ml of dry methylene chloride over 30 min. The mixture is stirred for additional 45 min. followed by addition of 10 ml of a dry methylene-chloride solution of 1.58 ml of geraniol. The resulting mixture is stirred at room temperature for 2.5 hours followed by addition of water. After separation of liquid layers the methylene chloride layer is washed with saturated aqueous sodium chloride and dried over anhydrous magnesium sulfate. The solvent is then distilled off under reduced pressure to give an oily product.

To a solution of 1.23 g of the residue obtained by the above procedures in 40 ml of methanol are added 10 ml of water and 280 mg of sodium carbonate. The mixture is stirred at room temperature for 5hours. After neutralized with 1N-hydrochloric acid, the solvent is distilled off under reduced pressure followed by extraction with two portions of methylene chloride. The methylene chloride layer is washed with saturated aqueous sodium chloride and dried over anhydrous magnesium sulfate. The solvent is then distilled off under reduced pressure, and the residue thus obtained is subjected to preparative thin layer chromatography developed with chloroform-methanol (100:1). The main band is eluted with 5% methanol-chloroform to obtain 670 mg of the desired product geranyl 5-(4-hydroxy-3-methoxyphenyl)-2,4-pentadienoate (8). Spectroscopic data of the product support the structure of the formula (8) below.

$^1$H NMR (CDCl$_3$, 60 MHz)δ:
1.48–1.84(9H), 1.93–2.22(4H), 3.82 (3), 4.71 (2H), 4.94–5.62 (2H), 5.93(1H), 6.56–7.68(6H)

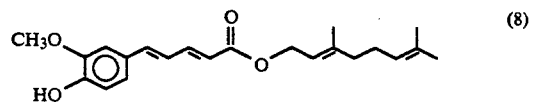

(8)

EXAMPLE 9

Under a nitrogen atmosphere, to a solution of 0.83 ml of ethyl chlorocarbonate in 75 ml of dry methylene chloride is dropwise added under ice-cooling a solution of 2.50 g of 5-(3,4-dimethoxymethoxyphenyl)-2,4-pentadienoic acid in 1.18 ml of triethylamine and 20 ml of dry methylene chloride over 30 min. The mixture is stirred for additional 30 min. followed by addition of 10 ml of a dry methylene chloride solution of 1.48 ml of geraniol. The resulting mixture is stirred at room temperature for 5 hours followed by addition of water. After separation of liquid layers the methylene chloride layer is washed successively with a saturated aqueous sodium hydrogen carbonate solution and saturated aqueous sodium chloride and dried over anhydrous magnesium sulfate. The solvent is then distilled off under reduced pressure to give an oily product.

To a solution of the residue obtained by the above procedures in 50 ml of methanol is added a catalytic amount of p-toluenesulfonic acid monohydrate. The mixture is stirred at 50° C. for 6 hours. The methanol is distilled off under reduced pressure, and the residue thus obtained is dissolved in 5% methanol-chloroform. The solution is washed with saturated aqueous sodium chloride and dried over anhydrous magnesium sulfate. The solvent is then distilled off under reduced pressure, and the residue thus obtained is subjected to preparative thin layer chromatography developed with chloroform-methanol (100:1). The main band is eluted with 5% methanol-chloroform to obtain 580 mg of the desired product geranyl 5-(3,4-dihydroxyphenyl)-2,4-pentadienoate (9). Spectroscopic data of the product support the structure of the formula (9) below.

$^1$H NMR (CDCl$_3$), DMSO—d$_6$ (60 MHz), δ:
1.52–1.80(9H), 1.93–2.26(4H), 4.60(2H), 4.86–5.53(2H), 5.87 (1H), 6.49–7.63 (6H)

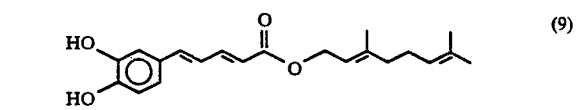

(9)

EXAMPLE 10

In 10 ml of methylene chloride is suspended 0.45 g of 5-(4-hydroxy-3 methoxyphenyl)-2,4-pentadienoic acid under an argon atmosphere. To the suspension cooled to −10° C. are added 0.58 ml of triethylamine and 0.39 ml of ethyl chlorocarbonate. To the mixture, after stirred for 30 min., is added a solution of 0.41 g of farnesol in methylene chloride, and the resulting mixture is stirred at −10° C. to 0° C. for 3 hours. The reaction mixture is poured onto water and extracted with chloroform. The organic layer is washed with saturated aqueous sodium chloride and dried over anhydrous sodium sulfate. The solvent is then distilled off under reduced pressure, and the residue is subjected to column chromatography on silica gel. From the fraction eluted with chloroform is obtained 0.38 g of franesyl 5-(4-ethoxycarbonyloxy-3-methoxyphenyl)-2,4-pentadienoate.

To a solution of 0.38 g of farnesyl 5-(4-ethoxycarbonyloxy-3-methoxyphenyl)-2,4-pentadienoate in 10 ml of methanol are added 2 ml of water and 0.08 g of sodium carbonate followed by stirring for 3 hours. To the reaction mixture is added 10 ml of water. The mixture is acidified with 1N hydrochloric acid and then extracted with chloroform. The organic layer is washed with saturated aqueous sodium chloride and dried over anhydrous sodium sulfate. The solvent is then distilled off under reduced pressure, and the residue is subjected to column chromatography on silica gel. From the fraction eluted with chloroform is obtained 0.22 g of farnesyl 5-(4-hydroxy-3-methoxyphenyl)-2,4-pentadienoate (10). Spectroscopic data of the product support the structure of the formula (10) below.

NMR (CDCl$_3$)δ:
5.93(1H,d,J=15 Hz), 4.71(2H,d,J=7 Hz), 4.26(2H,g,J=7 Hz), 3.87(3H,s), 1.35(3H,t,J=7 Hz)

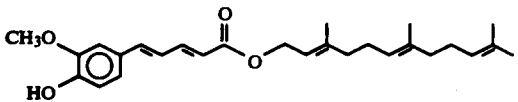

(10)

EXAMPLE 11

In 50 ml of ethanol are dissolved under an argon atmosphere 10.05 g of N-prenylphthalimide and 2.92 g of 80% hydrazine hydrate, and the solution is refluxed for 2 hours. To the reaction mixture is added 5 ml of concentrated hydrochloric acid. Precipitated crystals are filtered and washed with 4 portions of 5 ml of ethanol. The filtrate and the washings are combined, and the solvent is distilled off under reduced pressure to approximately 10 ml. To the residue is added 50 ml of water followed by filtration. The solvent is distilled off from the filtrate under reduced pressure. There is obtained prenylamine hydrochloride, to which are added 7 ml of a 40% aqueous solution of sodium hydroxide and then potassium carbonate to saturation. The organic layer is separated and dried over sodium hydroxide. There is obtained 1.30 g of prenylamine.

In 50 ml of methylene chloride is suspended 2.20 g of 5-(4'-hydroxy 3'-methoxyphenyl)pentadienoic acid under an argon atmosphere. To the suspension cooled to −10° C. are added 2.92 ml of triethylamine and 2.16 g of ethyl chlorocarbonate. To the mixture, after stirred for one hour, is added a solution of 1.28 g of prenylamine in 10 ml of methylene chloride, and the resulting mixture is stirred at −10° C. to 0° C. for 3 hours. The reaction mixture is poured onto water and extracted with chloroform. The organic layer is washed with saturated aqueous sodium chloride and dried over anhydrous sodium sulfate. The solvent is then distilled off under reduced pressure, and the residue is subjected to column chromatography on silica gel. From the fraction eluted with methylene chloride-methanol (99:1) is obtained 2.91 g of 5-(4'-ethoxycarbonyloxy-3'-methoxyphenyl)pentadienoic acid prenylamide.

To a solution of 1.34 g of 5-(4'-ethoxycarbonyloxy-3'-methoxyphenyl)pentadienoic acid prenylamide in 10 ml of methanol are added 2.8 ml of 2N aqueous solution of sodium hydroxide followed by stirring at room temperature for 15 min. The mixture is acidified with 1N hydrochloric acid and then extracted with chloroform. The organic layer is washed with water and dried over anhydrous sodium sulfate. The solvent is then distilled off under reduced pressure, and the residue is subjected to column chromatography on silica gel. From the fraction eluted with methylene chloride is obtained 0.77 g of 5-(4'-hydroxy-3'methoxyphenyl)pentadienoic acid prenylamide (11). Spectroscopic data of the product support the structure of the formula (11) below.

NMR (CDCl$_3$)δ:
5.96(1H,d,J=15 Hz), 3.91(2H,t,J=8 Hz), 3.77(3H,s), 1.66(6H,bs)

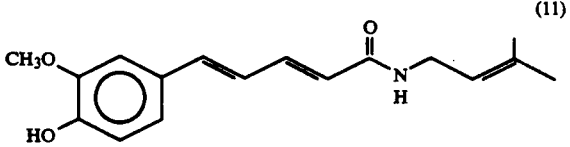

(11)

EXAMPLE 12

A solution of 3.00 g of N-geranylphthalimide and 0.80 g of 80% hydrazine hydrate in 60 ml of ethanol is refluxed for 3 hours. The solvent is distilled off under reduced pressure to afford a mixture of geranylamine and hydrazide.

Separately, 2.33 g of 5-(4'-hydroxy-3'-methoxyphenyl)pentadienoic acid is suspended in 50 ml of methylene chloride under an argon atmosphere. To the suspension cooled to −10° C. are added 2.95 ml of triethylamine and 2.03 ml of ethyl chlorocarbonate. To the mixture, after stirred for 30 min., is added a suspension of the geranylamine-hydrazide mixture in methylene chloride. The resulting mixture is stirred at −10° C. to 0° C. for 4 hours. The reaction mixture is filtered, and precipitates are washed with methylene chloride. Combined filtrate and washing are washed successively with water and saturated aqueous sodium chloride and dried over anhydrous sodium sulfate. The solvent is distilled off under reduced pressure, and the residue is subjected to column chromatography on silica gel. From the fraction eluted with chloroform is obtained 2.61 g of 5-(4'-ethoxycarbonyloxy-3'methoxyphenyl)pentadienoic acid geranylamide.

To a solution of 1.61 g of 5-(4'-ethoxycarbonyloxy-3'-methoxyphenyl)pentadienoic acid geranylamide in 25 ml of methanol is added 10 ml of 2N aqueous solution of sodium hydroxide. The mixture is stirred at room temperature for one hour. The reaction mixture, after acidified with 1N hydrochloric acid, is extracted with chloroform. The organic layer is washed with water and dried over sodium sulfate. The solvent is distilled off under reduced pressure, and the residue is subjected to column chromatography on silica gel. From the fraction eluted with methylene chloride is obtained 1.20 g of 5-(4'-hydroxy-3-methoxyphenyl)pentadienoic acid geranylamide (12). Spectroscopic data of the product support the structure of the formula (12) below.

NMR (CDCl$_3$)δ:
5.83(1H,d,J=15 Hz), 3.83(3H,s), 1.65(6H,s), 1.57(3H,s)

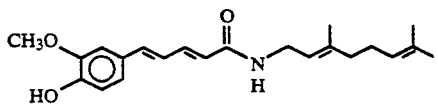

(12)

EXAMPLE 13

A solution of 2.10 g of (E,E)-N-farnesylphthalimide and 0.49 g of hydrazine hydrate in 40 ml of ethanol is refluxed for 3 hours. The solvent is distilled off under reduced pressure to afford a mixture of (E,E)farnesylamine and hydrazide.

Separately, 1.32 g of 5-(4'-hydroxy-3'-methoxyphenyl)pentadienoic acid is suspended in 30 ml of methylene chloride under an argon atmosphere. To the suspension cooled to −10° C. are added 1.67 ml of triethylamine and 1.15 ml of ethyl chlorocarbonate. To the mixture, after stirred for 30 min., is added a suspension of the (E,E)-farnesylamine-hydrazide mixture in methylene chloride. The resulting mixture is stirred at −10° C. to 0° C. for 3 hours. The reaction mixture is filtered, and precipitates are washed with methylene chloride. Combined filtrate and washing are washed with water, then with saturated aqueous sodium chloride and dried over anhydrous sodium sulfate. The solvent is distilled off under reduced pressure, and the residue is subjected to column chromatography on silica gel. From the fraction eluted with methylene chloride is obtained 2.06 g of 5-(4'-ethoxycarbonyloxy- 3'-methoxyphenyl)pentadienoic acid (E,E)-farnesylamide.

To a solution of 2.06 g of 5-(4'-ethoxycarbonyloxy-3'-methoxyphenyl)pentadienoic acid (E,E)-farnesylamide in 40 ml of methanol is added 20 ml of 2N aqueous solution of sodium hydroxide. The mixture is stirred at room temperature for one hour. The reaction mixture, after acidified with 1N hydrochloric acid, is extracted with chloroform. The organic layer is washed with water and dried over sodium sulfate. The solvent is distilled off under reduced pressure, and the residue is subjected to column chromatography on silica gel. From the fraction eluted with chloroform is obtained 1.67 g of 5-(4'-hydroxy3'-methoxyphenyl)pentadienoic acid (E,E)-farnesylamide (13). Spectroscopic data of the product support the structure of the formula (13) below.

NMR (CDCl$_3$)δ:
5.81(1H,d,J=15 Hz), 3.83(3H,s), 1.64(6H,bs), 1.55(6H,bs)

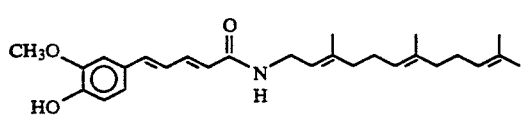

(13)

EXAMPLE 14

A solution of 2.62 g of N-geranylphthalimide and 0.70 g of hydrazine hydrate in 40 ml of ethanol is refluxed for 3 hours. The solvent is distilled off under reduced pressure to afford a mixture of geranylamine and hydrazide.

Separately, 1.80 g of ferulic acid is suspended in 40 ml of methylene chloride under an argon atmosphere. To the suspension cooled to −10° C. are added 2.58 ml of triethylamine and 1.77 ml of ethyl chlorocarbonate. To the mixture, after stirred for 30 min., is added a suspension of the geranylamine-hydrazide mixture in methylene chloride. The resulting mixture is stirred at −10° C. to 0° C. for 3 hours. The reaction mixture is filtered, and precipitates are washed with methylene chloride. Combined filtrate and washing are washed with water, then with saturated aqueous sodium chloride and dried over anhydrous sodium sulfate. The solvent is distilled off under reduced pressure, and the residue is subjected to column chromatography on silica gel. From the fraction eluted with methylene chloride is obtained 1.44 g of 4-ethoxycarbonyloxy-3-methoxycinnamic acid geranylamide.

To a solution of 1.44 g of 4-ethoxycarbonyloxy-3-methoxycinnamic acid geranylamide in 25 ml of methanol is added 10 ml of 2N aqueous solution of sodium hydroxide. The mixture is stirred at room temperature for one hour. The reaction mixture, after acidified with 1N hydrochloric acid, is extracted with chloroform. The organic layer is washed with water and dried over anhydrous sodium sulfate. The solvent is distilled off under reduced pressure, and the residue is subjected to column chromatography on silica gel. From the fraction eluted with chloroform is obtained 0.70 g of 4-hydroxy-3-methoxycinnamic acid geranylamide (14). Spectroscopic data of the product support the structure of the formula (14) below.

NMR (CDCl$_3$)δ:
7.45(1H,d,J=15 Hz), 6.21 (1H,d,J=15 Hz), 3.73(3H,s), 1.70(6H,bs), 1.50(3H,bs)

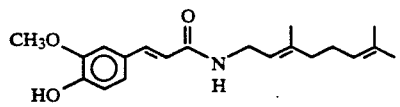

(14)

EXAMPLE 15

A solution of 2.50 g of N-geranylphthalimide and 0.66 g of hydrazine hydrate in 50 ml of ethanol is refluxed for 3 hours. The solvent is distilled off under reduced pressure to afford a mixture of geranylamine and hydrazide.

Separately, 2.60 g of 5-(3',4'-dimethoxymethoxyphenyl)pentadienoic acid is suspended in 30 ml of methylene chloride under an argon atmosphere. To the suspension cooled to −10° C. are added 1.23 ml of triethylamine and 0.85 ml of ethyl chlorocarbonate. To the mixture, after stirred for 30 min., is added a suspension of the geranylamine-hydrazide mixture in methylene chloride. The resulting mixture is stirred at −10° C. to 0° C. for 3 hours. The reaction mixture is filtered, and precipitates are washed with methylene chloride. Combined filtrate and washing are washed with water, then with saturated aqueous sodium chloride and dried over anhydrous sodium sulfate. The solvent is distilled off under reduced pressure, and the residue is subjected to column chromatography on silica gel. From the fraction eluted with chloroform is obtained 2.12 g of 5-(3',4'-dimethoxymethoxyphenyl)pentadienoic acid geranylamide.

To a solution of 1.96 g of 5-(3',4'-dimethoxymethoxyphenyl)pentadienoic acid geranylamide in 40 ml of methanol is added 0.09 g of p-toluenesulfonic acid monohydrate. The mixture is stirred at 50° C. for 3 hours. The reaction mixture is poured onto water and extracted with chloroform. The organic layer is washed with saturated aqueous sodium chloride and dried over anhydrous sodium sulfate. The solvent is distilled off under reduced pressure, and the residue is subjected to column chromatography on silica gel. From the fraction eluted with chloroform-methanol (99:1) is obtained 1.40 g of 5-(3',4'-dihydroxyphenyl)pentadienoic acid geranylamide (15). Spectroscopic data of the product support the structure of the formula (15) below.

NMR (CDCl$_3$)$\delta$:
5.81(1H,d,J=15 Hz), 1.63(6H,s), 1.57(3H,s)

37° C. for 15 min. To the reaction mixture, after ice-cooling, is added one drop of 1N HCl (hydrochloric acid), and the resulting mass is extracted with 2 ml of ethyl acetate. The extract is concentrated to dryness followed by addition of 100 μl of methanol for use as a test specimen.

Said specimen is injected into octadecylsilane (ODS) reverse phase high performance liquid chromatography (HPLC), eluted with methanol - acetonitrile - water - acetic acid (15 : 45 : 35 : 0.01). Peak for 5-HETE (5-(s)-hydroxy-6,8,11,14-eicosatetraenoic acid), a 5-lipoxygenase product detected in approximately 25 min. is measured. The 5-lipoxygenase-inhibiting activity is determined by decrease in the peak for said 5-lipoxygenase product. As a result of the test remarkable 5-lipoxygenase-inhibiting activities were found as shown in Table 1 below. It was demonstrated that isoprenoid derivatives of the invention not shown in Table 1 also have a high 5-lipoxygenase-inhibiting activity.

TALBE 1

| Structural formula | Example No. | 50% Inhibitory concentration (mole) |
|---|---|---|
| CH$_3$O-, HO- phenyl-CH=CH-CH=CH-C(=O)-CH$_2$-CH=C(CH$_3$)$_2$ | 1 | 5.0 × 10$^{-7}$ |
| CH$_3$O-, HO- phenyl-CH=CH-CH=CH-C(=O)-CH$_2$-CH$_2$-CH=C(CH$_3$)-CH$_2$-CH=C(CH$_3$)$_2$ (geranyl ketone) | 2 | 3.8 × 10$^{-7}$ |
| CH$_3$O-, HO- phenyl-CH=CH-CH=CH-C(=O)-(farnesyl) | 3 | 8.0 × 10$^{-7}$ |
| HO-, HO- phenyl-CH=CH-C(=O)-CH$_2$-CH$_2$-CH=C(CH$_3$)$_2$ | 4 | 8.0 × 10$^{-8}$ |

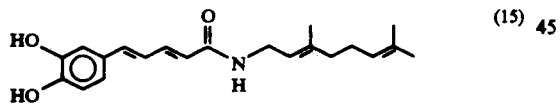

(15)

TEST EXAMPLE 1

5-Lipoxygenase-inhibiting activity

A suspension of rat-origin basophilic leukemia cell strain RBL-1 in an Eagle basal medium (manufactured by Gibco Laboratories) containing 10% FCS is cultivated in an 5% CO$_2$ incubator at 37° C. The culture is then centrifuged at 4° C. to collect cells. The cells are re-suspended in a phosphate buffer solution at pH 7.4 to a cell density of 1.0–3.0×10$^7$ cells/ml. The suspended cells are treated by an ultrasonic cell blender and then centrifuged at 15,000 rpm at 4° C. for 30 min. The supernatant is employed as an enzyme solution of a 5-lipoxygenase. In test tubes are placed 50 μg of arachdonic acid and an isoprenoid derivative of the invention to be tested. To each of the test tubes are added 0.30 ml of phosphate buffer, 0.20 ml of the enzyme solution as prepared above and 5 μl of a 100 mM CaCl$_2$ (calcium chloride) solution. The mixture is allowed to react at

TEST EXAMPLE 2

5-Lipoxygenase-inhibiting activity

A suspension of rat-origin basophilic leukemia cell strain RBL-1 in an Eagle basal medium (manufactured by Gbco Laboratories) containing 10 % FCS is cultivated in a 5% CO$_2$ incubator at 37° C. The culture is then centrifuged at 4° C. to collect cells. The cells are re-suspended in a phosphate buffer solution at pH 7.4 to a cell density of 1.0 –3.0×10$^7$ cells/ml. The suspended cells are treated by an ultrasonic cell blender and then centrifuged at 15,000 rpm at 4° C. for 30 min. The supernant is employed as an enzyme solution of a 5-lipoxygenase. In test tubes are placed 20 μl of radiolabeled arachidonic acid (10 μl Ci/ml) and an isoprenoid derivative of the invention to be tested. To each of the test tubes are added 0.40 ml of phosphate buffer, 0.10 ml of the enzyme solution as prepared above and 5 ml of a 100 mM CaCl$_2$ (calcium chloride). The mixture is allowed to react at 37° C. for 15 min. To the reaction mixture, after ice-cooling, is added one drop of 1N HCl (hydrochloric acid), and the resulting mass is extracted with 2 ml of ethyl acetate. The extract is concentrated, and the concentrate is spotted and developed on a silica gel thin layer plate (Merck 60F$_{254}$). Measurement of the inhibitory activity is accomplished by collecting the portion corresponding to 5-HETE (5-(s)-hydroxy-6,8,11,14-eicosatetraenoic acid), a 5-lipoxygenase product detected by a radio-thin layer chromatogram scanner (Dünnschicht-Scanner II LB2723, manufactured by Berthold) and measuring radioactivity by a liquid scintillation counter. The 5-lipoxygenase-inhibiting activity is determined by decrease in the production of said 5-lipoxygenase product. As a result of the test remarkable 5-lipoxygenase-inhibiting activities were found as shown in Table 2 below. It was demonstrated that isoprenoid derivatives of the invention not shown in Table 2 also have a high 5-lipoxygenase-inhibiting activity.

nase as described above to 50% by introducing said isoprenoid derivative when production of 5-HETE without isoprenoid derivative of the invention is taken as 100%.

TEXT EXAMPLE 3
Anti-ulcer activity

To male Wistar rats (weighing 150–200 g) fasted for 24 hours was administered orally an isoprenoid derivative of the invention. One hour later, ethanol-hydrochloric acid (containing 150 mM hydrochloric acid in 60% ethanol) was orally given in a volume of 0.5 ml/100 g bodyweight.

One hour later, the animals were sacrificed with

TABLE 2

| Structural formula | Example No. | 50% Inhibitory concentration (mole) |
|---|---|---|
| (CH₃O, HO-phenyl cinnamate prenyl ester) | 5 | $3.0 \times 10^{-6}$ |
| (CH₃O, HO-phenyl dienoate prenyl ester) | 6 | $4.0 \times 10^{-7}$ |
| (HO, HO-phenyl dienoate prenyl ester) | 7 | $2.6 \times 10^{-8}$ |
| (CH₃O, HO-phenyl cinnamate geranyl ester) | 8 | $1.2 \times 10^{-6}$ |
| (HO, HO-phenyl dienoate geranyl ester) | 9 | $2.6 \times 10^{-7}$ |
| (CH₃O, HO-phenyl dienamide prenyl) | 11 | $6.5 \times 10^{-7}$ |
| (CH₃O, HO-phenyl dienamide geranyl) | 12 | $8.3 \times 10^{-8}$ |
| (CH₃O, HO-phenyl dienamide farnesyl) | 13 | $3.1 \times 10^{-7}$ |
| (CH₃O, HO-phenyl cinnamamide geranyl) | 14 | $9.2 \times 10^{-7}$ |
| (HO, HO-phenyl dienamide geranyl) | 15 | $1.1 \times 10^{-8}$ |

50% inhibitory concentration as referred to in Tables 1 and 2 means concentration of an isoprenoid derivative required for controlling the production of 5lipoxygeether. The stomach was excised and, after formalin treatment, measured for the length (mm) of lesions developed in glandular portions of the stomach. Total length of the lesions per animal was taken as ulcer index.

As shown in Table 3, marked anti-ulcer activities were found in the test. It was demonstrated that isoprenoid derivatives of the invention not shown in Table 3 also have a similar anti-ulcer activity.

TABLE 3

| Example No. | Anti-ulcer activity | |
| --- | --- | --- |
| | Dose | Percent inhibition of ulceration |
| 1 | 100 mg/kg | 79.3% |
| 2 | " | 94.6% |
| 3 | " | 85.0% |

Percent inhibition of ulceration as referred to in the table is a value indicating the ulcer index for the rat without an isoprenoid derivative of the invention orally given minus the ulcer index for the orally administered rat divided by the ulcer index for the orally non-administered rat multiplied by 100.

ACUTE TOXICITY

An acute toxicity test was run in ICR male mice (5 week-old) by oral administration. $LD_{50}$ value of any of the compounds of the invention was more than 2000 mg/kg, which was high in ratio to effective dose and thereby demonstrated high safety.

INDUSTRIAL APPLICABILITY

According to the present invention there are provided novel isoprenoid derivatives and 5-lipoxygenase inhibitors and anti-ulcer agents containing the same.

Said compounds of the invention have been found to have a 5-lipoxygenase-inhibiting activity and an anti-ulcer activity. Thus, said compounds can inhibit the action of 5-lipoxygenase thereby inhibiting production of leukotrienes such as $LTC_4$ and $LTD_4$ which are formed by the action of 5-lipoxygenase. Accordingly, said isoprenoid derivatives can effectively be used as a 5-lipoxygenase inhibitor in such diseases as gastritis, hepatitis, rheumatism and gastric ulcer as well as asthma and rhinitis of allergic diseases.

As the compounds of the invention can inhibit ulceration, they are effective for use as a therapeutic agent for gastric and other ulcers.

Therefore, the invention is applicable in the field of pharmaceutical industry.

We claim:

1. An isoprenoid derivative represented by the general formula (I)

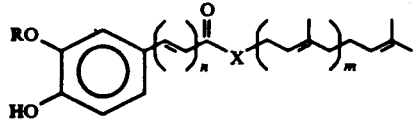

(I)

wherein R represents a hydrogen atom or a lower alkyl group, X represents —CH$_2$—[, —O—] or —NH—, n represents number of double bonds in transconfiguration and is 1 or 2, and m is an integer from 0 to 3.

2. The isoprenoid derivative according to claim 1, wherein said lower alkyl group is methyl, ethyl, n-propyl, i-propyl and n-butyl.

3. The isoprenoid derivative according to claim 2, wherein said lower alkyl group is methyl.

4. The isoprenoid derivative represented by the general formula (I) according to claim 1, wherein n represents number of double bonds in trans-configuration and is 2.

5. The isoprenoid derivative represented by the general formula (I) according to claim 1, wherein m is an integer from 1 to 3.

6. An isoprenoid derivative represented by the general formula (I)

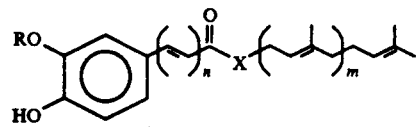

(I)

wherein R represents a lower alkyl group, X represents —CH$_2$— or —NH—, n represents number of double bonds in trans-configuration and is 2 and m is an integer from 1 to 3.

7. A pharmaceutical composition for the inhibition of 5-lipoxygenase, said composition comprising the isoprenoid derivative of the general formula (I) according to claim 1 and a pharmaceutically acceptable carrier therefor.

8. The pharmaceutical composition for the inhibition of 5-lipoxygenase according to claim 7, wherein said lower alkyl group is methyl, ethyl, n-propyl, i-propyl and n-butyl.

9. The pharmaceutical composition for the inhibition of 5-lipoxygenase according to claim 7, wherein said lower alkyl group is methyl.

10. The pharmaceutical composition for the inhibition of 5-lipoxygenase according to claim 7, wherein n represents number of bond double in trans-configuration and is 2.

11. The pharmaceutical composition for the inhibition of 5-lipoxygenase according to claim 7, wherein m is an integer from 1 to 3.

12. The pharmaceutical composition for the inhibition of 5-lipoxygenase, said composition comprising the isoprenoid derivative of the general formula (I) according to claim 6 and a pharmaceutically acceptable carrier therefor.

13. The pharmaceutical composition for the prevention or treatment of an ulcer in a mammal, said composition comprising the isoprenoid derivative of the general formula (I) according to claim 1 and a pharmaceutically acceptable carrier therefor.

14. The pharmaceutical composition for the prevention or treatment of an ulcer in a mammal according to claim 13, wherein said lower alkyl group is methyl, ethyl, n-propyl, i-propyl and n-butyl.

15. The pharmaceutical composition for the prevention or treatment of an ulcer in a mammal according to claim 13, wherein said lower alkyl group is methyl.

16. The pharmaceutical composition for the prevention or treatment of an ulcer in a mammal according to claim 13, wherein n represents number of double bonds in trans-configuration and is 2.

17. The pharmaceutical composition for the prevention or treatment of an ulcer in a mammal according to claim 13, wherein m is an integer from 1 to 3.

18. The pharmaceutical composition for the prevention or treatment of an ulcer in a mammal, said composition comprising the isoprenoid derivative of the general formula (I) according to claim 6 and a pharmaceutically acceptable carrier therefor.

19. A method for the inhibition of 5-lipoxygenase in a mammal comprising administering to a mammal in need of such treatment an effective amount to inhibit 5-lipoxygenase of an isoprenoid derivative of the general formula (I) according to claim 1.

20. The method for the inhibition of 5-lipoxygenase according to claim 19, wherein said lower alkyl group is methyl, ethyl, n-propyl, i-propyl and n-butyl.

21. The method for the inhibition f 5-lipoxygenase according to claim 19, wherein said lower alkyl group is methyl.

22. The method for the inhibition of 5-lipoxygenase according to claim 19, wherein n represents number of double bonds in trans-configuration and is 2.

23. The method for the inhibition of 5-lipoxygenase according to claim 19, wherein m is an integer from 1 to 3.

24. A method for the inhibition of 5-lipoxygenase in a mammal comprising administering to a mammal in need of such treatment an effective amount to inhibit 5-lipoxygenase of an isoprenoid derivative of the general formula (I) according to claim 6.

25. A method for the prevention or treatment of an ulcer in a mammal comprising administering to a mammal in need of such treatment an effective amount to prevent or treat an ulcer of an isoprenoid derivative of the general formula (I) according to claim 1.

26. The method of the prevention or treatment of an ulcer according to claim 25, wherein said lower alkyl group is methyl, ethyl, n-propyl, i-propyl and n-butyl.

27. The method of the prevention or treatment of an ulcer according to claim 25, wherein said lower alkyl group is methyl.

28. The method of the prevention or treatment of an ulcer according to claim 25, wherein n represents number of double bonds in trans-configuration and is 2.

29. The method for the prevention or treatment of an ulcer according to claim 25, wherein m is an integer from 1 to 3.

30. The method for the prevention or treatment of an ulcer in a mammal in need of such treatment in an effective amount to prevent or treat an ulcer of an isoprenoid derivative of the general formula (I) according to claim 6.

* * * * *